US009017996B2

(12) United States Patent
Fujimoto

(10) Patent No.: US 9,017,996 B2

(45) Date of Patent: Apr. 28, 2015

(54) BACTERIA ANALYZER, METHOD FOR ANALYZING BACTERIA, AND A COMPUTER PROGRAM PRODUCT

(75) Inventor: Yukie Fujimoto, Kobe (JP)

(73) Assignee: Sysmex Corporation (JP)

( * ) Notice: Subject to any disclaimer, the term of this patent is extended or adjusted under 35 U.S.C. 154(b) by 728 days.

(21) Appl. No.: 12/589,891

(22) Filed: Oct. 29, 2009

(65) Prior Publication Data

US 2010/0112623 A1 May 6, 2010

(30) Foreign Application Priority Data

Oct. 30, 2008 (JP) ................................ 2008-279008
Aug. 14, 2009 (JP) ................................ 2009-187935

(51) Int. Cl.

*G01N 33/493* (2006.01)
*G01N 21/47* (2006.01)
*G01N 33/569* (2006.01)
*G01N 15/14* (2006.01)

(52) U.S. Cl.

CPC ...... *G01N 33/56911* (2013.01); *G01N 15/1425* (2013.01); *G01N 15/1459* (2013.01); *G01N 33/493* (2013.01); *G01N 2015/1486* (2013.01); *Y10S 435/808* (2013.01)

(58) Field of Classification Search

CPC .......... G01N 33/493; G01N 33/56911; G01N 15/1459; G01N 2015/1486; G01N 15/1425; G01N 15/0211; G01N 2015/0238; G01N 21/47; G01N 2021/4702

See application file for complete search history.

(56) References Cited

U.S. PATENT DOCUMENTS

| | | | | |
|---|---|---|---|---|
| 5,935,804 | A * | 8/1999 | Laine et al. | 435/18 |
| 7,309,581 | B2 * | 12/2007 | Sakai et al. | 435/40.5 |
| 2002/0006631 | A1 * | 1/2002 | Houwen et al. | 435/7.24 |
| 2004/0067548 | A1 * | 4/2004 | Kawashima et al. | 435/34 |
| 2004/0219627 | A1 | 11/2004 | Kawashima | |
| 2009/0081770 | A1 * | 3/2009 | Srienc et al. | 435/289.1 |
| 2010/0075369 | A1 * | 3/2010 | Godefroy et al. | 435/39 |

FOREIGN PATENT DOCUMENTS

EP 1136563 A2 9/2001

* cited by examiner

*Primary Examiner* — Nathan Bowers

(74) *Attorney, Agent, or Firm* — Brinks Gilson & Lione

(57) ABSTRACT

A bacteria analyzer comprising: a sample preparing section for preparing a measurement sample from a specimen; a detector for detecting bacteria contained in the measurement sample prepared by the sample preparing section; and a controller including a memory under control of a processor, the memory storing instructions enabling the processor to carry out operations, comprising: obtaining the distribution state of bacteria detected by the detector; setting a bacteria count region according to the obtained bacteria distribution state; and counting the number of bacteria contained in the set bacteria count region is disclosed. Method for analyzing bacteria, and a computer program product for bacteria analyzer are also disclosed.

10 Claims, 11 Drawing Sheets

START
S1101 Obtain measurement data
S1102 Generate scattergram
S1103 Calculate distribution width DW and mean value M of the forward scattered light
S1104 Mean≧W? (YES / NO)
S1105 DW<X? (YES / NO)
S1106 Set 3rd count region as the bacteria count region
S1107 Set 1st count region as the bacteria count region
S1108 Count bacteria in the bacteria count region
S1109 Display the scattergram and bacteria count
END

| Type | Bacteria count [/mL] | | | Viable count [cfu/mL] |
|---|---|---|---|---|
| | 1st count region | 2nd count region | Output value | |
| E. coli | 1.7E+08 | 0.1E+08 | 1.6E+08 | 1.9E+08 |
| Bacillus sp. | 2.5E+07 | 0.1E+07 | 2.4E+07 | 2.3E+07 |
| Pseudomonas aeruginosa | 1.4E+08 | 1.3E+08 | 1.4E+08 | 1.9E+08 |
| Staphylococcus aureus | 6.1E+07 | 1.6E+07 | 6.1E+07 | 2.6E+07 |

FIG. 8

| Sample 1 | Bacteria count | $1^{st}$ setting method | $2^{nd}$ setting method | $3^{rd}$ setting method | |
|---|---|---|---|---|---|
| | 5.5E+05 | 5.4E+05 | 5.4E+05 | 5.4E+05 | Bacteria count [/mL] |
| | | 13% | 98% | 98% | Vs. Viable count |

| Sample 2 | Bacteria count | $1^{st}$ setting method | $2^{nd}$ setting method | $3^{rd}$ setting method | |
|---|---|---|---|---|---|
| | 5.5E+05 | 1.7E+06 | 2.8E+07 | 2.8E+07 | Bacteria count [/mL] |
| | | 3% | 51% | 51% | Vs. Viable count |

| Sample 3 | Bacteria count | $1^{st}$ setting method | $2^{nd}$ setting method | $3^{rd}$ setting method | |
|---|---|---|---|---|---|
| | 1.5E+08 | 2.4E+07 | 1.2E+08 | 1.2E+08 | Bacteria count [/mL] |
| | | 16% | 83% | 83% | Vs. Viable count |

- $1^{st}$ setting method: set $3^{rd}$ count region f.
- $2^{nd}$ setting method: determine distribution width DW, set $1^{st}$ count region h
- $3^{rd}$ setting method: determine distribution width (use width of 60% of the maximum point in the histogram), set $1^{st}$ count region h

FIG. 10

BACTERIA ANALYZER, METHOD FOR ANALYZING BACTERIA, AND A COMPUTER PROGRAM PRODUCT

RELATED APPLICATIONS

This application claims priority under 35 U.S.C. §119 to Japanese Patent Application No. 2008-279008 filed on Oct. 30, 2008 and Japanese Patent Application No. 2009-187935 filed on Aug. 14, 2009, the entire content of which is hereby incorporated by reference.

FIELD OF THE INVENTION

The present invention relates to a bacteria analyzer, a method for analyzing bacteria, and a computer program product for analyzing bacteria contained in a sample such as blood, urine and the like.

BACKGROUND

Conventional bacteria analyzers are known for analyzing bacteria contained in samples such as blood, urine and the like using flow cytometry (for example, refer to EP1136563, U.S. Laid-Open Patent No. 2004-219627).

The bacteria detection method disclosed in EP1136563 creates a two-dimensional distribution diagram based on a combination of the forward scattered light intensity and the forward scattered light pulse width. Groups including bacteria are identified using the two-dimensional distribution diagram, and a new two-dimensional diagram is created based on the combination of the forward scattered light intensity and the fluorescent light intensity only for the identified groups. In this way bacteria can be separated from other components (crystals, broken cells and other impurities) according to the differences in fluorescent light intensity, and the number of bacteria can be more precisely counted.

The bacteria measuring method disclosed in U.S. Laid-Open Patent No: 2004-219627 differentiates bacilli and cocci based on differences of slope in the bacteria distribution states. In order to distinguish between bacteria and other components (crystals, broken cells and other impurities), a scattergram is prepared beforehand by plotting the forward scattered light intensity and fluorescent light intensity on the two axes and presetting the range in which bacteria appear in the scattergram, then counting the number of particles appearing within the set range as the number of bacteria.

The ranges in which bacteria appear in the scattergram differ greatly depending on the type of bacteria and state of proliferation. There are therefore normally circumstances under which a large number of bacteria may appear in a region in which impurities appear depending on the type of bacteria and state of proliferation. In the disclosures of EP1136563 and U.S Laid-Open Patent No. 2004-219627, however, a large number of bacteria may appear in region with impurities when a fixed region is set as the bacteria count region regardless of the type of bacteria and state of proliferation, such that there is need for improved precision in the bacteria count because in such instances bacteria in the impurity region may be excluded from the count object.

SUMMARY

The scope of the invention is defined solely by the appended claims, and is not affected to any degree by the statements within this summary.

A first aspect of the invention is a bacteria analyzer comprising: a sample preparing section for preparing a measurement sample from a specimen; a detector for detecting bacteria contained in the measurement sample prepared by the sample preparing section; and a controller including a memory under control of a processor, the memory storing instructions enabling the processor to carry out operations, comprising: obtaining the distribution state of bacteria detected by the detector; setting a bacteria count region according to the obtained bacteria distribution state; and counting the number of bacteria contained in the set bacteria count region.

A second aspect of the invention is a bacteria analyzer comprising: a sample preparing section for preparing a measurement sample from a specimen; a detector for detecting bacteria contained in the measurement sample prepared by the sample preparing section; an obtaining means for obtaining the distribution state of bacteria detected by the detector; a setting means for setting a bacteria count region according to the obtained bacteria distribution state; and a counting means for counting the number of bacteria contained in the set bacteria count region.

A third aspect of the invention is method for analyzing bacteria capable of being performed by a bacteria analyzer, the analyzer comprising a sample preparing section for preparing a measurement sample, and a detector for detecting bacteria contained in the measurement sample prepared by the sample preparing section, comprising: obtaining the distribution state of bacteria detected by the detector; setting a bacteria count region according to the obtained bacteria distribution state; and counting the number of bacteria contained in the set bacteria count region.

A fourth aspect of the invention is a computer program product for a bacteria analyzer comprising a sample preparing section for preparing a measurement sample and a detector for detecting the bacteria contained in the measurement sample prepared by the sample preparing section, the computer program product comprising a computer readable medium storing instructions adapted to enable a bacteria analyzer to carry out operations, comprising: obtaining the distribution state of bacteria detected by the detector; setting a bacteria count region according to the obtained bacteria distribution state; and counting the number of bacteria contained in the set bacteria count region.

BRIEF DESCRIPTION OF THE DRAWINGS

FIG. 8 is a comparison of a viable count by culture method and bacteria count in a first count region and a second count region;

FIG. 9A is based on a scattergram obtained from a measurement sample containing Escherichia coli (E. coli);

FIG. 9B is based on a scattergram obtained from a measurement sample containing Bacillus bacteria;

FIG. 9C is based on a scattergram obtained from a measurement sample containing Pseudomonas aeruginosa;

FIG. 9D is based on a scattergram obtained from a measurement sample containing Staphylococcus aureus;

FIG. 10 compares the results of counting bacteria present in bacteria count regions set by three setting methods and a general viable count by culture method using Heart-Infusion agar medium and urine samples collected from three patients.

DETAILED DESCRIPTION OF THE PREFERRED EMBODIMENTS

Hereinafter, embodiments of a sample analyzer of the invention will be described in detail with reference to the accompanying drawings.

The bacteria analyzer of the present embodiment is described below by way of example of a urine analyzer for analyzing urine with specific reference to the drawings.

Figure 1:
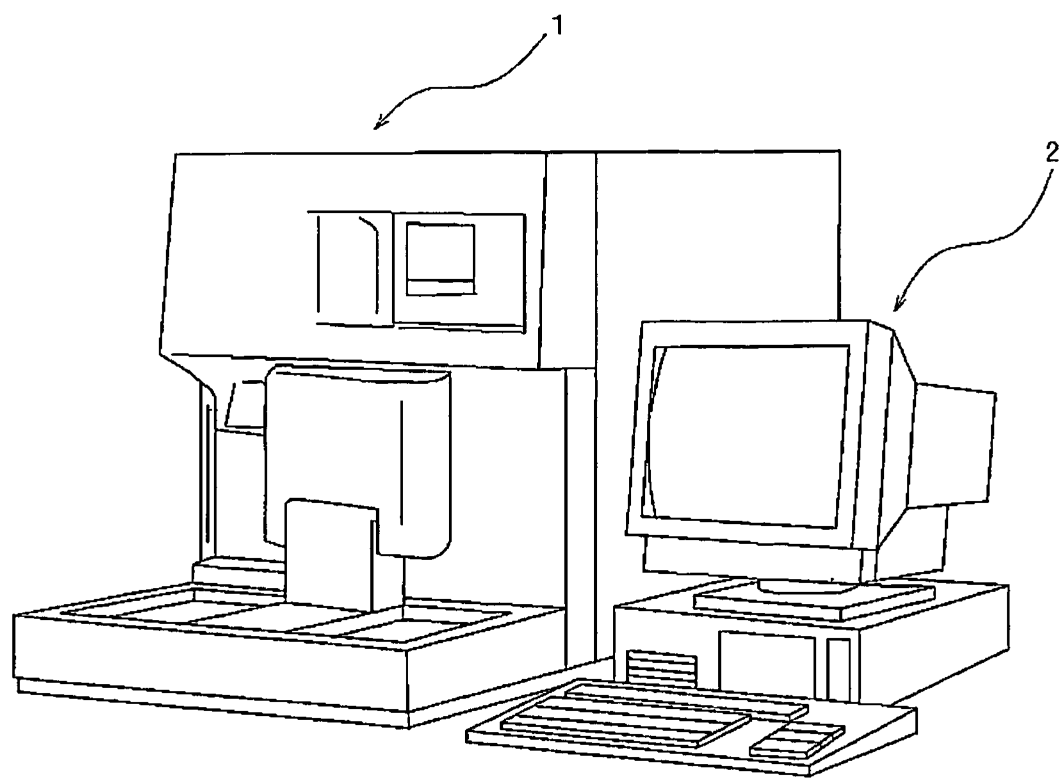
FIG. 1 is a perspective view schematically showing an embodiment of the bacteria analyzer of the present invention.

FIG. 1 is a perspective view schematically showing an embodiment of the bacteria analyzer of the present invention. As shown in FIG. 1, the bacteria analyzer of the present embodiment is configured by a measuring device 1, and an operation and display device 2 which is connected to the measuring device 1 so as to be capable of data communication.

The measuring device 1 and the operation and display device 2 are connected via a communication line, which is not shown in the drawing, so that the operation of the measuring device 1 can be controlled and measurement data output from the measuring device 1 can be processed to obtain analysis results by mutual data communication. The measuring device 1 and the operation and display device 2 may also be connected over a network, integratedly configured as a single apparatus, and transfer data in inter-process communication.

The measuring device 1 detects the bacteria in a sample (urine) using flow cytometry, and transmits the detection result to the operation and display device 2 as measurement data. Flow cytometry is a method for detecting particles (bacteria) in a measurement sample by creating a sample flow containing a measurement sample, irradiating the sample flow with laser light, and detecting the light, such as forward scattered light, side scattered light, and side fluorescent light emitted from the particles (bacteria) in the measurement sample. For example, the particles (bacteria) distributed in a scattergram can be counted using a scattergram (two-dimensional distribution diagram) prepared by plotting the forward scattered light intensity and side fluorescent light intensity on the two axes.

Specifically, a predetermined region in which the bacteria are concentrated in the distribution of the scattergram is set as the bacteria count region, and the particles (bacteria) appearing in the bacteria count region are counted. In the present embodiment, using a scattergram in which the forward scattered light intensity and side fluorescent light intensity are plotted on the two axes, the particles (bacteria) appearing in the set bacteria count region in the scattergram are counted.

Bacteria which may be present in urine include Escherichia coli, Bacillus species, Pseudomonas aeruginosa, Staphylococcus aureus and the like, which have different sizes and attributes. The type of bacteria present in the urine differs for each patient subject. The region in which the bacteria appear in the scattergram is different depending on the type of bacteria, and each type of bacterium has a characteristic occurrence pattern. In the present embodiment, the bacteria count region in the scattergram is set according to the bacteria appearance pattern in the scattergram, and the bacteria appearing in the set bacteria count region are counted.

Figure 2:
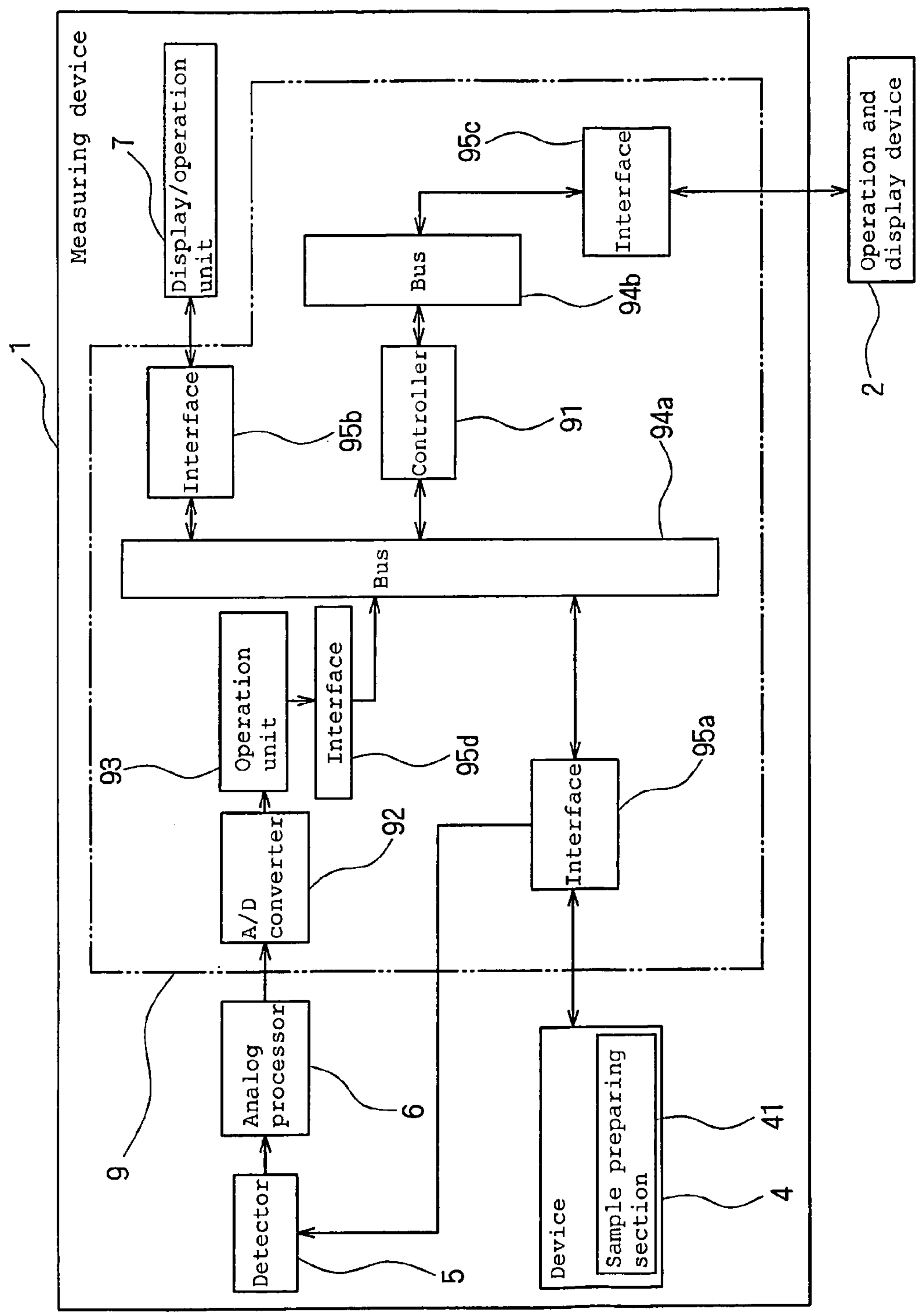
FIG. 2 is a block diagram showing the structure of the measuring device of the embodiment of the bacteria analyzer of the present invention.

FIG. 2 is a block diagram showing the structure of the measuring device 1 of the embodiment of the bacteria analyzer of the present invention. The measuring device 1 is provided with a device 4, detector 5 for performing the measurement of a measurement sample, an analog processor 6 for the output of the detector 5, operation and display section 7, and control board 9 for controlling the operation of each hardware part.

The control board 9 has a controller 91 with a control processor and a memory for operating the control processor, a 12-bit A/D converter 92 for converting the signals output from the analog processor 6 into digital signals, and an operation section 93 for storing the digital signals output from the A/D converter 92 and performing a process to select data output from the controller 91. The controller 91 is connected to the display/operation section 7 through a bus 94 and an interface 95*b*, and connected to the operation and display device 2 through a bus 94*b* and an interface 95*c*. The operation section 93 outputs an operation result to the controller 91 through an interface 95*d* and a bus 94*a*. The controller 91 also transmits the operation result (measurement data) to the operation and display device 2.

Figure 3:
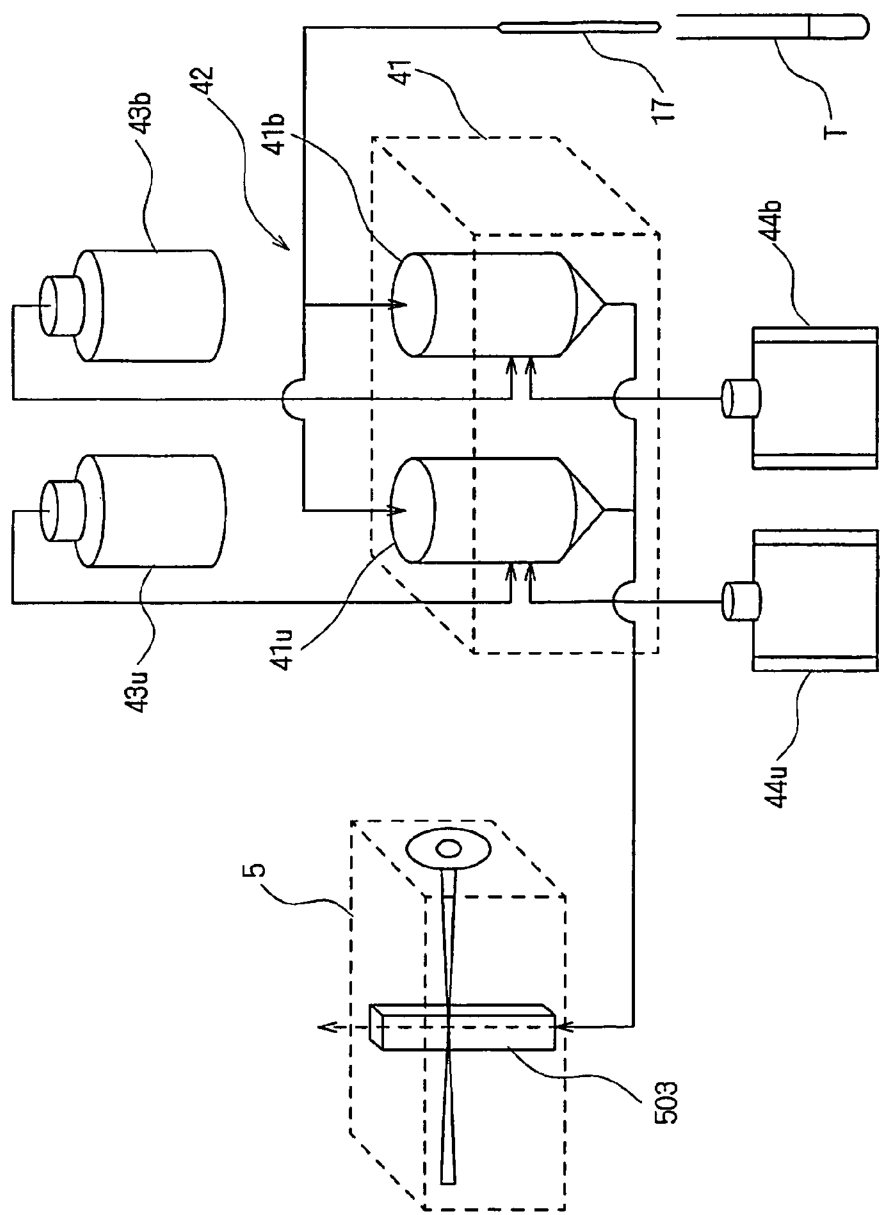
FIG. 3 is a block diagram schematically showing the structure of the detector and sample preparation section of the embodiment of the present invention.

The device 4 is provided with a sample preparing section 41 for preparing a measurement sample by fluorescent staining of a sample. The sample preparing section 41 prepares a bacteria count measurement sample. FIG. 3 is a block diagram schematically showing the structure of the detector 5 and sample preparation section 41 of the embodiment of the present invention.

In FIG. 3, the urine contained in the test tube T1 is aspirated by a syringe pump (not shown) using an aspirating tube 17, and then dispensed to the sample preparing section 41 by the sample distribution section 42. The sample preparing section 41 includes a first sample preparing unit 41*u* and a second sample preparing unit 41*b*. The first sample preparing unit 41*u* accommodates a first sedimentation aliquot for analyzing relatively large tangible components such as red blood cells, white blood cells, epithelial cells and the like; the second sample preparing unit 41*b* accommodates a second bacterial system aliquot for analyzing relatively small tangible components such as bacteria.

The urine dispensed to the first sample preparing unit 41*u* and the second sample preparing unit 41*b* is respectively diluted with diluting solution 43*u* and 43*b*, and mixed with a staining liquid (staining reagent) 44*u* and 44*b*. A suspension of the tangible components is prepared by respectively staining with the dye contained in the staining liquid 44*u* and 44*b*. The first sample preparing unit 41*u* prepares a first sample for measuring the tangible components containing at least white blood cells, and the second sample preparing unit 41*b* prepares a second sample for measuring bacteria.

Among the two types of suspensions (measurement samples) prepared in this manner, the suspension (first sample) prepared by the first sample preparing unit 41*u* is first delivered to the detector 5 where a sample flow encapsulated in added sheath fluid is irradiated by laser light in a sheath flow cell 503. Thereafter, the suspension (second sample) prepared by second sample preparing unit 41*b* is delivered to the detector 5 where a sample flow encapsulated in added sheath fluid is irradiated by laser light in the sheath flow cell 503. These operations are performed by operating drive units and electromagnetic valves (not shown) controlled by the controller 91.

Figure 4:
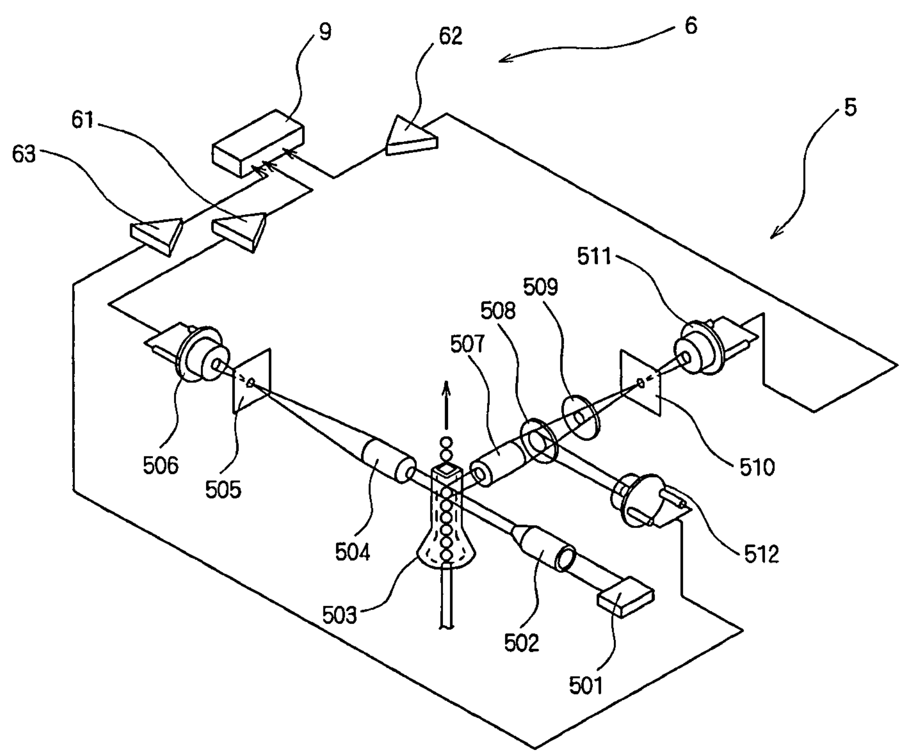
FIG. 4 is a block diagram schematically showing the analog processing unit and detector of the embodiment of the present invention.

FIG. 4 is a block diagram schematically showing the structure of the detector 5 and analog processor 6 of the embodiment of the present invention. As shown in FIG. 4, the detector 5 is configured by a light-emitter 501 for emitting laser light, irradiating lens unit 502, sheath flow cell 503 for irradiating with laser light, collective lens 504 disposed on a line extending in the direction of travel of the laser light emitted from the light-emitter 501, pinhole 505 and PD (photodiode) 506 (a beam stopper (not shown) is disposed between the sheath flow cell 503 and the collecting lens 504), collective lens 507 disposed in a direction intersecting the direction of travel of the laser light emitted from the light-emitter 501, dichroic mirror 508, optical filter 509, pinhole 510 and APD (avalanche photodiode) 511, and PD (photodiode) 512 disposed on the side of the dichroic mirror 508.

The light-emitter 501 is provided for emitting light on a sample flow containing a measurement sample passing through the interior of the sheath flow cell 503. The irradiating lens unit 502 is provided for rendering into parallel rays the light emitted from the light-emitter 501. The PD 506 is provided for receiving the forward scattered light emitted from the sheath flow cell 503. Note that information can be obtained relating to the size of the particles (blood cells) in the measurement sample from the forward scattered light emitted from the sheath flow cell 503.

The dichroic mirror 508 is provided for splitting the side scattered light and side fluorescent light emitted from the sheath flow cell 503. Specifically, the dichroic mirror 508 is provided for directing the side scattered light emitted from the sheath flow cell 503 to the PD 512, and directing the side fluorescent light emitted from the sheath flow cell 503 to the APD 511. The PD 512 is also provided for receiving the side scattered light. Information can be obtained relating to the size of the nucleus of a particle (blood cell) in the measurement sample from the side scattered light emitted from the sheath flow cell 503.

The APD 511 is also provided for receiving the side fluorescent light. When light irradiates a fluorescent substance such as a stained blood cell, light is produced that has a longer wavelength than the wavelength of the irradiating light. The fluorescent light intensity becomes stronger as the degree of staining increases. Therefore, the type and attributes of the bacteria can be specified by the side fluorescent light emitted from the sheath flow cell 503. The PD 506, PD 512, and APD 511 convert the respectively received light signal to an electrical signal, which is then respectively amplified by the amplifiers 61, 62, 63, and subsequently transmitted to the control board 9.

Figure 5:
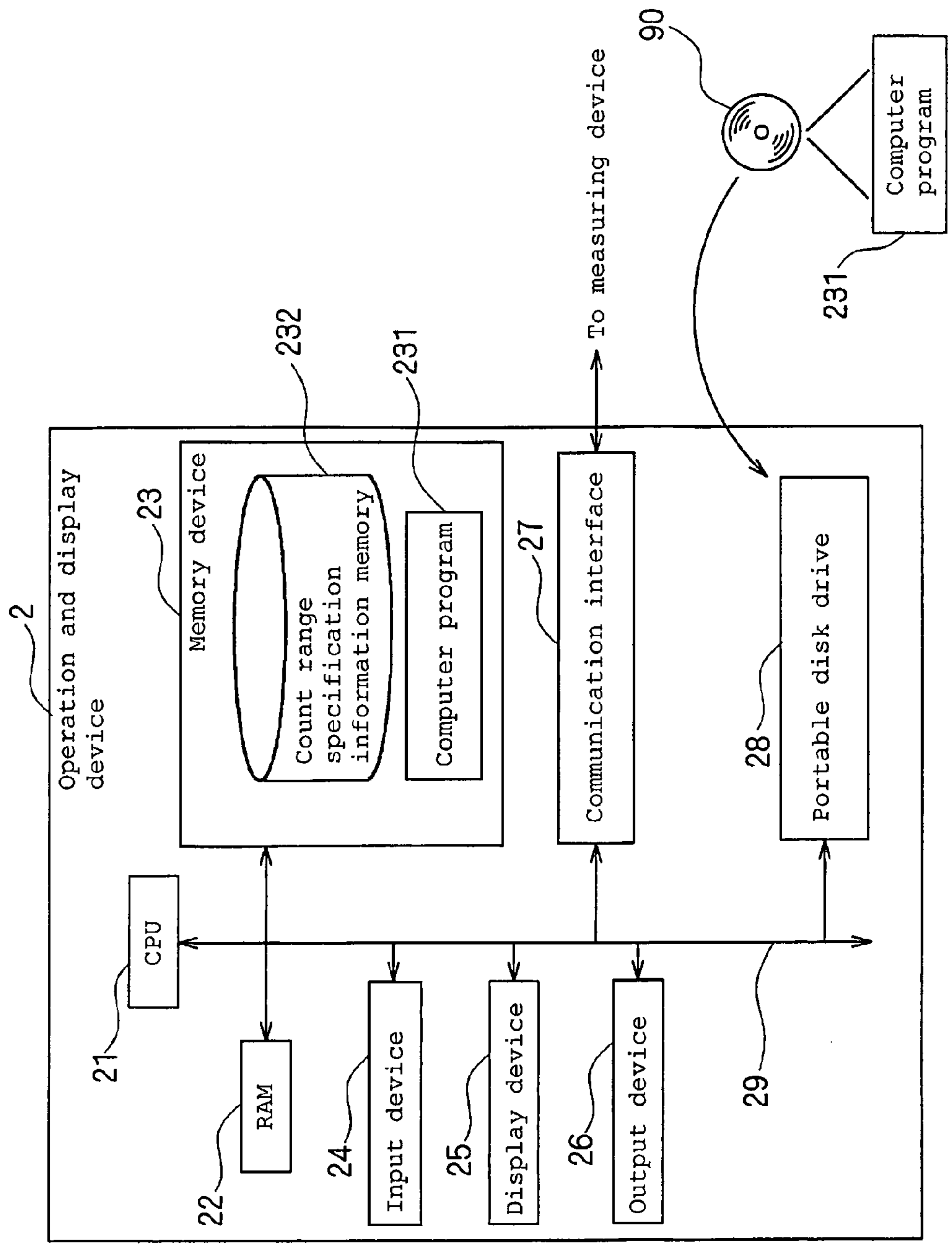
FIG. 5 is a block diagram showing the structure of the operation and display device of the embodiment of the bacteria analyzer of the present invention.

FIG. 5 is a block diagram showing the structure of the operation and display device 2 of the embodiment of the bacteria analyzer of the present invention. As shown in FIG. 5, the operation and display device 2 is configured by a CPU (central processing unit) 21, RAM 22, memory device 23, input device 24, display device 25, output device 26, communication interface 27, portable disk drive 28, and internal bus 29 connecting all the hardware. The CPU 21 is connected to each hardware part mentioned above of the operation and display device 2 via the internal bus 29; the CPU 21 controls the operation of these hardware parts, and executes the functions of various software in conjunction with a computer program 231 stored in the memory device 23. The RAM 22 is a volatile member configured by SRAM, SDRAM or the like, and is used for developing loaded modules during the execution of the computer program 231, and for storing temporary data during the execution of the computer program 231.

The memory device 23 is configured by an internal ROM, fixed-type storage device (hard disk) or the like. The computer program 231 stored on the memory device 23 may be downloaded from a portable storage medium 90 such as a DVD, CD-ROM or the like for recording information such as programs and data, then expanded from the memory device 23 to the RAM22 during execution. Of course, the computer program may also be downloaded from an external computer connected to a network through the communication interface 27. The memory device 23 is also provided with a count range specification information memory 232 for storing count range specification information, which is information necessary for specifying a count range. Information for decision parameters such as the range of mean values of the forward scattered light intensity, distribution width threshold values, and threshold values of the side fluorescent light intensity for exclusion from the count range may be stored as count range specification information.

The communication interface 27 is connected to the internal bus 29, and is capable of sending and receiving data via the connection with the measuring device 1 over the communication line. That is, instruction information specifying to start a measurement and the like is transmitted to the measuring device 1, and measurement data are received.

The input device 24 is a data input medium such as a keyboard and mouse. The display device 25 is a CRT monitor, LCD or the like, and displays analysis results graphically. The output device 26 is a printing device such as a laser printer, inkjet printer or the like.

Figure 6:
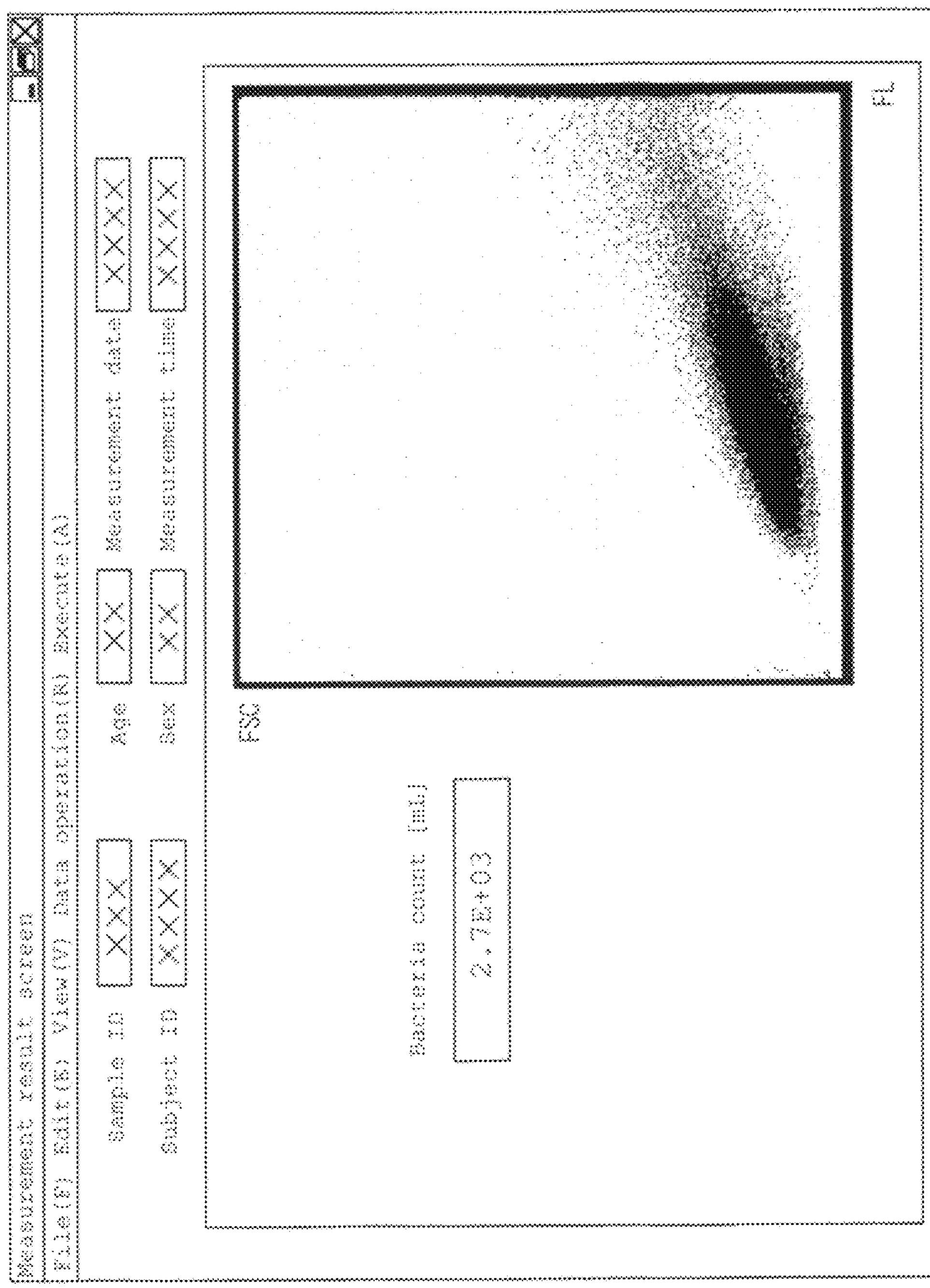
FIG. 6 shows an example of a bacteria measurement result screen displayed on the operation and display device.
Figure 7A:
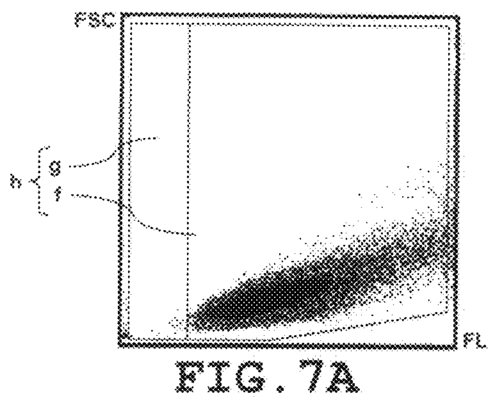
FIG. 7A is a scattergram obtained from a measurement sample containing Escherichia coli (E. coli)
Figure 7B:
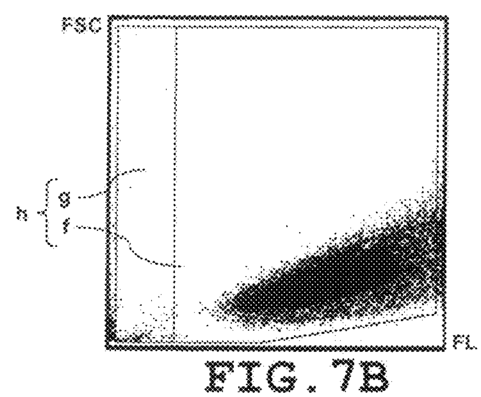
FIG. 7B is a scattergram obtained from a measurement sample containing Bacillus bacteria.
Figure 7C:
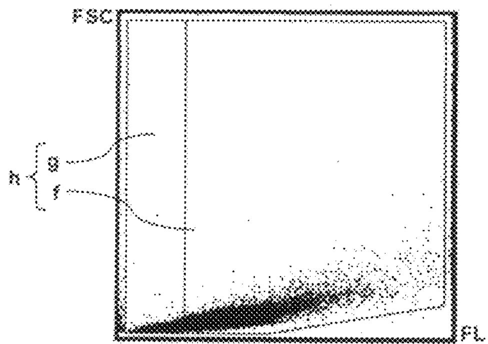
FIG. 7C is a scattergram obtained from a measurement sample containing Pseudomonas aeruginosa.
Figure 7D:
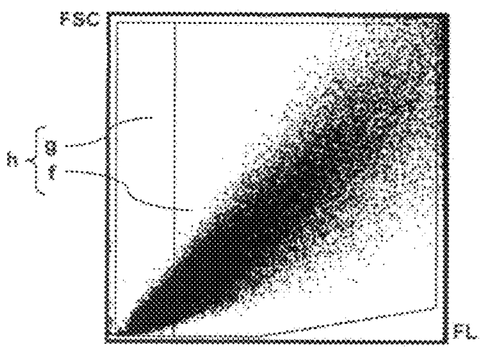
FIG. 7D is a scattergram obtained from a measurement sample containing Staphylococcus aureus.
Figure 9A:
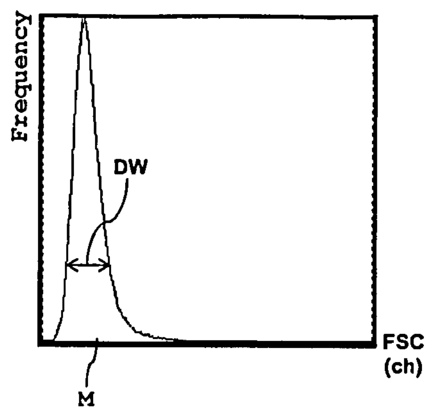
FIGS. 9A through 9D show examples of the relationship between the count number and the forward scattered light intensity in a scattergram.
Figure 9B:
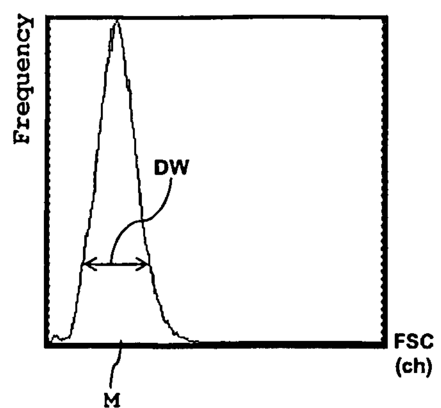
Figure 9C:
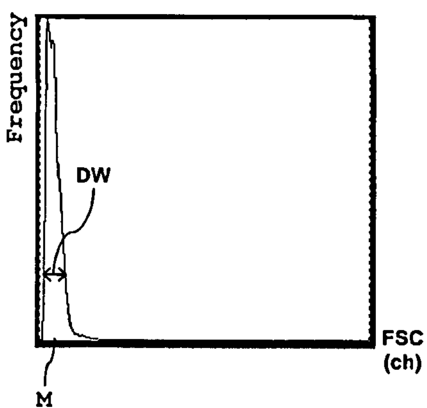
Figure 9D:
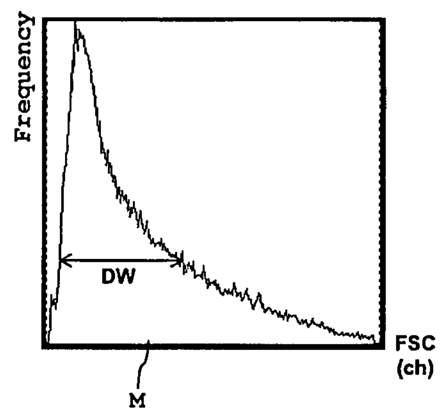

The operation of the bacteria analyzer with the above-mentioned structure is described below. When the bacteria analyzer of the present embodiment counts the bacteria contained in urine, the operation and display device 2 prepares a scattergram based on the measurement data from the measuring device 1, counts the detected number of bacteria (number of particles) based on the prepared scattergram, and displays the result on the display device. FIG. 6 shows an example of a bacteria measurement result screen displayed on the operation and display device 2.

In the scattergram shown in FIG. 6, the forward scattered light intensity (FSC) is plotted on the vertical axis and the side fluorescent light intensity (FL) is plotted on the horizontal axis. The bacteria count is the total counted number of bacteria appearing in the set bacteria count region when the bacteria count region has been set in the scattergram according to the appearance pattern of the bacteria in the scattergram.

The bacteria count region set according to the appearance pattern of the bacteria in the scattergram is described in detail below. As described above, the characteristic appearance pattern of the bacteria is shown in the scattergram according to the type of bacteria present in the urine of the subject because the type of bacteria present in the urine is different for each subject. FIG. 7 shows examples of scattergrams generated based on the measurement results of measurement samples respectively prepared from axenically cultured samples (culture solution) for four types of bacteria. FIG. 7(*a*) shows an example of a scattergram produced based on the measurement results of a measurement sample prepared from a sample of E. coli, FIG. 7(*b*) shows an example of a scattergram produced based on the measurement results of a measurement sample prepared from a sample of Bacillus sp., FIG. 7(*c*) shows an example of a scattergram produced based on the measurement results of a measurement sample prepared from a sample of Pseudomonas aeruginosa, and FIG. 7(*d*) shows an example of a scattergram produced based on the measurement results of a measurement sample prepared from a sample of Staphylococcus aureus.

In the scattergram shown in FIG. 7, the forward scattered light intensity (FSC) is plotted on the vertical axis and the side fluorescent light intensity (FL) is plotted on the horizontal axis. Note that the appearance patterns of the bacteria in the scattergrams are compared using the late stage of the logarithmic growth phase of the bacteria in the relationship between culturing time and the bacteria count. The late stage of the logarithmic growth phase is the phase of logarithmic division and propagation of bacteria, and is the stage prior to the end stage of the logarithmic growth phase before the stationary phase during which bacteria division and extinction attain equilibrium.

As shown in FIGS. 7(*a*) and 7(*b*), bacteria appear concentrated in a region of relatively high forward scattered light intensity and side fluorescent light intensity in the scattergrams generated based on the measurement results of the measurement samples respectively prepared from the E. coli and Bacillus sp. samples. This phenomenon is caused by the large sizes of the E. coli and Bacillus sp. bacteria, and indicates the same appearance pattern for similarly large bacteria.

As shown in FIGS. 7(*c*) and 7(*d*), bacteria appear concentrated in a region of low forward scattered light intensity and side fluorescent light intensity due to the small size of the Pseudomonas aeruginosa in the scattergrams generated based on the measurement results of the measurement samples respectively prepared from the Pseudomonas aeruginosa and Staphylococcus aureus samples. This phenomenon indicates the same appearance pattern for similarly small bacteria. The Staphylococcus aureus bacteria have variable size due to having botryoidal characteristics, and appear in a broad range from a region of low forward light intensity and side fluorescent light intensity to a region of high forward scattered light intensity and side fluorescent light intensity.

As shown in FIGS. 7(*a*) through 7(*d*), a first count region h and a second count region g are set in the scattergram as the bacteria count regions. The first count region h corresponds to a region composed of the combined second count region g and third count region f.

In the case of large size bacteria such as the E. coli and Bacillus sp. bacteria shown in FIGS. 7(*a*) and 7(*b*), the bacteria count value is the value of the total bacteria appearing in the third count region f from which the first count region h and the second count region g are excluded. In the case of small bacteria or variable size bacteria such as the Pseudomonas aeruginosa and Staphylococcus aureus bacteria shown in FIGS. 7(*c*) and 7(*d*), the bacteria count value is the total bacteria appearing in the first count region h.

FIG. 8 is a comparison of a viable count by culture method and bacteria count in the first count region h and the second count region g. FIG. 8 shows the examination results obtained using Bacillus sp. and Pseudomonas aeruginosa bacteria in the measurement samples among the scattergrams of FIG. 7 (FIGS. 7(*b*) and (*c*)). The viable count by culture method was counted using the samples (media) used in the measurement sample from which the scattergrams of FIG. 7 were obtained. The output values in FIG. 8 respectively represent the bacteria count of the first count region h in the case of Pseudomonas aeruginosa bacteria, and the value after subtracting the bacteria count of the second count region g from the bacteria count of the first count region h in the case of Bacillus sp. bacteria. Note that when counting bacteria, a correction is added to the appropriate count region by excluding the region of high probability that no bacteria will appear in the first count region h and second count region g of FIG. 7.

As shown in FIG. 8, in the case of large size bacteria such as Bacillus sp., the output value (2.4E+07) is understood to approach the viable count (2.3E+07) by subtracting the bacteria count (0.1E+07) of the second count region g from the bacteria count (2.5E+07) of the first count region h. Therefore, large size bacteria can be counted with high precision by counting the bacteria appearing in the third count region f obtained by excluding the second count region g from which the first count region h.

In the case of small size bacteria such as Pseudomonas aeruginosa, the output value (1.4E+08) is understood to approach the viable count (1.9E+08) by not subtracting the bacteria count (1.3E+08) of the second count region g from the bacteria count (1.4E+08) of the first count region h. Therefore, small size bacteria can be counted with high precision by counting the bacteria appearing in the first count region without excluding the second count region g from the first count region h.

The standard for setting the bacteria count region (first count region h or second count region g) for counting bacteria from the appearance pattern in the scattergram is described below.

FIG. 9 is a histogram showing the relationship between the count value and the forward scattered light intensity in each scattergram of FIG. 7. FIG. 9(*a*) shows the relationship between the count value and the forward scattered light intensity in the basic measurement result produced from the E. coli scattergram of FIG. 7(*a*), FIG. 9(*b*) shows the relationship between the count value and the forward scattered light intensity in the basic measurement result produced from the Bacillus sp. scattergram of FIG. 7(*b*), FIG. 9(*c*) shows the relationship between the count value and the forward scattered light intensity in the basic measurement result produced from the Pseudomonas aeruginosa scattergram of FIG. 7(*c*), and FIG. 9(*d*) shows the relationship between the count value and the forward scattered light intensity in the basic measurement result produced from the Staphylococcus aureus scattergram of FIG. 7(*d*),In FIG. 9, the count value is plotted on the vertical axis and the forward scattered light intensity (FSC) is plotted on the horizontal axis.

As shown in FIG. 9, large size bacteria such as E. coli and Bacillus sp. shown in FIGS. 9(*a*) and 9(*b*) have larger mean values Mean for the forward scattered light intensity (FSC) than the small size bacteria such as Pseudomonas aeruginosa shown in FIG. 9(*c*). Variable size bacteria such as Staphylococcus aureus shown in FIG. 9(*d*) have larger mean values for the forward scattered light intensity (FSC) than the small size bacteria similar to the large size bacteria. However, variable size bacteria such as shown in FIG. 9(*d*) can be distinguished from the large size bacteria because the forward scattered light intensity distribution width DW, which reflects the size of variation, is larger than that of the large size bacteria shown in FIGS. 9(*a*) and 9(*b*). Therefore, a bacteria count region corresponding to the bacteria appearance pattern can be set based on the forward scattered light intensity distribution width DW and the mean value M of the forward scattered light intensity (FSC).

Specifically, the bacteria are large size bacteria such as E. coli and Bacillus sp. when the mean value M of the forward scattered light intensity is large and the forward scattered light intensity distribution width DW is small. In this case, the a large number of bacteria appear in the region of relatively high fluorescent light intensity in the scattergram and few bacteria appear in the second count region g of relatively low fluorescent light intensity, as shown in FIGS. 7(*a*) and 7(*b*). Therefore, the bacteria count is accomplished by counting the bacteria appearing in the third count region f obtained by excluding the second count region g from the first count region h.

Small size bacteria such as Pseudomonas aeruginosa are present when the mean value M of the forward scattered light intensity is small and the forward scattered light intensity distribution width DW is small. In this case, a large amount of bacteria appear in the region of low forward scattered light intensity and a large amount of bacteria appear in the second count region g, as shown in FIG. 7(*c*). Therefore, the bacteria count is accomplished by counting the bacteria appearing in the first count region h including the second count region g.

Bacteria are variable size bacteria such as Staphylococcus aureus when the mean value M of the forward scattered light intensity if large and the forward scattered light intensity distribution width DW is also large. In this case, bacteria appear over a large region from the region of relatively low side fluorescent light intensity in the scattergram, and a large amount of bacteria appear in the second count region g, as shown in FIG. 7(*d*). Therefore, the bacteria count is accomplished by counting the bacteria appearing in the first count region h including the second count region g.

The measurement samples prepared from the urine of a plurality of subjects are then measured using the bacteria analyzer of the present embodiment, and the bacteria count is compared to a viable count by the culture method. Three setting methods are used as the method for setting the bacteria count region for counting the number of bacteria. The culture method uses two types of culture, that is, CLED agar medium and Heart-Infusion agar medium.

The first setting method sets the first count region h for all measurement samples. The second setting method sets the threshold of the mean value M of the forward scattered light intensity as W(ch), and sets the threshold of the distribution width DW of the forward scattered light intensity as X(ch). Measurement samples with a mean value M equal to or greater than the threshold value W and a distribution width DW less than X are set to the third count region f, and measurement samples with a mean value M less than W and measurement samples with a mean value M equal to or greater than W and a distribution width DW equal to or greater than X are set to the first count region h. The third setting method sets the distribution width DW at 60% of the lateral of the maximum count position of the histogram, sets the threshold value of the mean value M as Y, and sets the threshold value of the distribution width DW as Z. Measurement samples with a mean value M equal to or greater than Y and a distribution width DW less than Z are set to the third count region f, and measurement samples with a mean value M less than Y and measurement samples with a mean value M equal to or greater than Y and a distribution width DW equal to or greater than Z are set to the first count region h.

Note that the threshold value W of the mean value M, and the threshold values X and Z of the distribution width DW are respectively set, for example, at values 20 ch, 30 ch, 45 ch, 60 ch and the like when values 0 to 255 are channel (ch) values as in the present embodiment. The threshold values W, Y, X, and Z are pre-stored, as information required for setting the count range, in the count range characteristic information memory 232 of the memory device 23 of the operation and display device 2.

FIG. 10 compares the results of counting bacteria present in bacteria count regions set by three setting methods and a general viable count by culture method using Heart-Infusion agar medium and urine samples collected from three patients. As shown in FIG. 10, regarding sample 1, the count result was 13% according to the first setting method when the count result of the viable count by culture method was 100%, whereas the count result was 98% using the second setting method and 98% using the third setting method, by which methods the count result approaches the viable count.

Regarding the second sample, the count result was 3% according to the first setting method when the count result of the viable count by culture method was 100%, whereas the count result was 51% using the second setting method and 51% using the third setting method, by which methods the count result approaches the viable count.

Regarding the third sample, the count result was 16% according to the first setting method when the count result of the viable count by culture method was 100%, whereas the count result was 83% using the second setting method and 83% using the third setting method, by which methods the count result approaches the viable count.

These results prove it is possible to obtain values near the viable count by the culture method by setting the bacteria count region based on the second and third setting methods and counting the bacteria present within the set bacteria count region.

Figure 11:
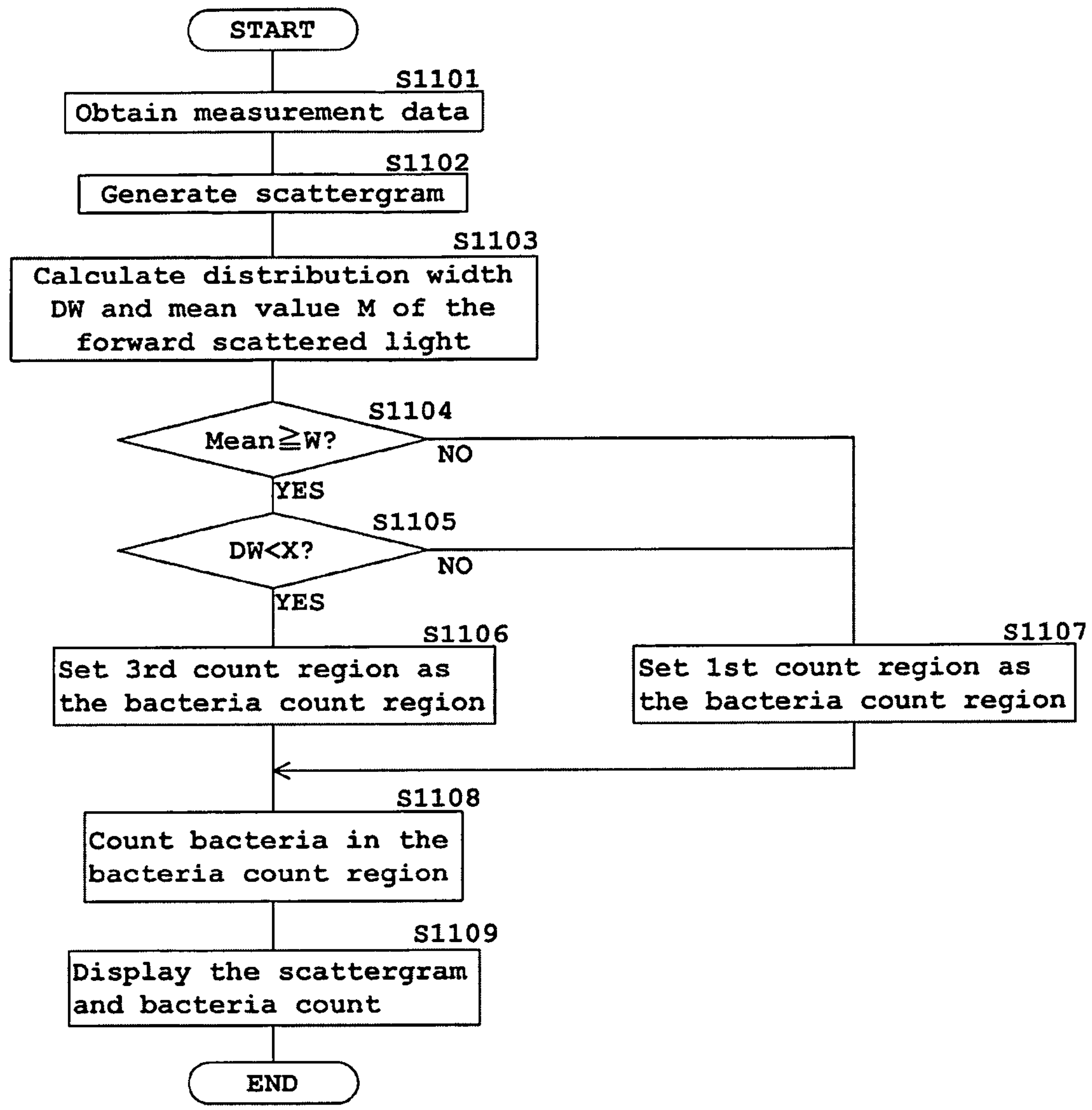
FIG. 11 is a flow chart showing the sequence of the bacteria counting process performed by the CPU of the operation and display device of the embodiment of the bacteria analyzer of the present invention.

FIG. 11 is a flow chart showing the sequence of the bacteria counting process performed by the CPU 21 of the operation and display device 2 of the embodiment of the bacteria analyzer of the present invention. FIG. 11 illustrates the processing when the bacteria count region is set according to the third setting method.

The CPU 21 of the operation and display device 2 obtains the measurement data from the measuring device 1 (step S1101), and creates a scattergram (step S1102). In the present embodiment, the scattergram is generated by plotting the forward scattered light on the vertical axis and plotting the side fluorescent light on the horizontal axis.

The CPU 21 calculates the mean value M and the distribution width DW of the forward scattered light intensity (step S1103). The method of calculating the distribution width DW is not specifically limited. In the present embodiment, the distribution width DW is calculated as the width of the forward scattered light intensity at a height (count number) equivalent to "20" when the maximum height (maximum count number) in the histogram of the forward scattered light intensity is designated "100."

The CPU 21 determines whether the mean value M of the forward scattered light intensity is equal to or greater than the threshold W ($0<W<255$) (step S1104). When the CPU 21 has determined that the mean value M of the forward scattered light intensity is equal to or greater than the threshold value W (step S1104: YES), the CPU 21 then determines whether the distribution width DW of the forward scattered light intensity is less than the threshold X ($0<X<255$) (step S1105).

When the CPU 21 has determined that the distribution width DW of the forward scattered light intensity is less than the threshold value X (step S1105: YES), the CPU 21 then sets the third count region f, that is the region obtained by excluding the second count region g from the first count region h, as the bacteria count region (step S1106).

When the CPU has determined that the mean value M of the forward scattered light intensity is less than the threshold value W (step 51104: NO), or when the distribution width DW of the forward scattered light intensity is equal to or greater than the threshold value X and the mean value M of the forward scattered light intensity is equal to or greater than W (step S1105: NO), the CPU 21 sets the first count region h as the bacteria count region (step S1107).

The CPU 21 counts the bacteria included in the set bacteria count region (step S1108), and displays the scattergram and the calculated bacteria count on the display device 25 (step S1109).

According to the embodiment described above, the bacteria count region can be set as the count target according to the bacteria distribution state on the scattergram, particles other than bacteria can be prevented from inflating the count value by effectively excluding a region containing particles such as impurities that are not bacteria, and undercounting the bacteria count by excluding from the count target a region in which bacteria are actually present can be prevented before such exclusion occurs. Therefore, highly accurate count values can be obtained, and a bacteria analyzer capable of performing high precision analysis can be provided.

Note that although the above embodiment is described by way of example of a bacteria analyzer capable of detecting and counting both bacteria and tangible components in urine, the present invention is not specifically limited to this example inasmuch as the present invention is also applicable to an apparatus capable of detecting and counting only bacteria, and a bacteria analyzer for analyzing bacteria contained in other samples such as blood without limitation to urine. Although the setting of the bacteria count region changes based on the distribution width and mean value of the forward scattered light intensity which functions as information relating to bacteria size, the present invention is not limited to this arrangement. For example, rather than the mean value of the forward scattered light intensity, the value of the forward scattered light intensity at the peak of the distribution of the forward scattered light intensity may also be used. As a further example, the standard deviation of the forward scattered light intensity distribution may also be used in place of the distribution width DW which reflects the variation in the size of the bacteria. As a still further example, the setting of the bacteria count region may also be set based on the distribution width and mean value of the side fluorescent light intensity which functions as information relating to the attributes of the bacteria.

Although the above embodiment is described by way of example in which the bacteria count region is selected from a first count region h and a third count region f, the present invention is not limited to this arrangement. For example, a suitable bacteria count region may be set according to the bacteria distribution state, and the bacteria present in the set bacteria counting region may be counted.

Although the above embodiment is described by way of example in which the forward scattered light intensity and the side fluorescent light intensity are used when generating a scattergram for representing the bacteria distribution state, the present invention is not limited to this arrangement. For example, the forward scattered light intensity and the side fluorescent light intensity may be used, and the width of the light signals may be used rather than the light intensity.

Moreover, the present invention is not limited to the above embodiment, and may be variously modified and transposed insofar as such modifications and transpositions do not depart from the scope of the present invention.

What is claimed is:

1. A bacteria analyzer comprising:

a sample preparing section that prepares a measurement sample by mixing a specimen containing bacteria and a fluorescent dye;

a flow cell through which the measurement sample passes;

a light source that irradiates the measurement sample passing the flow cell;

a first detector that detects light scattered from a bacterium in the measurement sample and outputs a first signal according to an intensity of scattered light;

a second detector that detects fluorescence of the bacterium in the measurement sample and outputs a second signal according to an intensity of fluorescence;

a controller including a memory under control of a processor, the memory storing a first threshold value of a mean value of the first signal and a second threshold value of a degree of variation of the first signal, wherein the controller is programmed to perform instructions comprising:

obtaining a mean value and a degree of variation of the first signal of at least some of the bacteria in the measurement sample, wherein the mean value and the degree of variation of the first signal are determined from a histogram defining relationship between the magnitude of the first signal and a frequency of bacteria;

generating a scattergram by plotting the first and the second signals on first and second axes of the scattergram, wherein the first axis represents a magnitude of the first signal and the second axis represents a magnitude of the second signal;

defining a first bacteria count region from the scattergram if the mean value of the first signal is less than the first threshold value, or the degree of the variation of the first signal is greater than the second threshold value, the first bacteria count region comprising a first counting region which contains a second counting region near the origin of the scattergram;

defining a second bacteria count region from the scattergram if the mean value of the first signal is equal to or greater than the first threshold value and the degree of the variation of the first signal is less than the second threshold value, the second bacteria count region comprising a third counting region from which the second counting region is excluded; and counting plots in the first or second bacteria count region defined as a total number of bacteria.

2. The analyzer of claim 1, wherein the second counting region is defined as a region having a coordinate lower than a predetermined coordinate with respect to the second axis.

3. The analyzer of claim 1, wherein the degree of the variation of the first signal is a width of a histogram of the first signal at a height of certain percentage of a maximum height of the histogram.

4. The analyzer of claim 1, wherein the degree of the variation of the first signal is a standard deviation of the first signal.

5. The analyzer of claim 1, wherein the specimen is urine.

6. The analyzer of claim 1, wherein the sample preparing section includes:

a first sample preparing unit for accommodating a first aliquot used to analyze red blood cells in a urine, and a second sample preparing unit for accommodating a second aliquot used to analyze bacteria in a urine, and the analyzer further comprises a sample distribution section that dispenses a first aliquot of a urine to the first sample preparing unit and a second aliquot of the urine to the second sample preparing unit.

7. The analyzer of claim 1, wherein the bacteria comprises *E. Coli* and the controller is programmed to count a number of *E. Coli* in the specimen.

8. The analyzer of claim 1, wherein the bacteria comprises *Bacillus* sp. and the controller is programmed to count a number of *Bacillus* sp. in the specimen.

9. The analyzer of claim 1, wherein the bacteria comprises *Pseudomonas aeruginosa* and the controller is programmed to count a number of *Pseudomonas aeruginosa* in the specimen.

10. The analyzer of claim 1, wherein the bacteria comprises *Staphylococcus aureus* and the controller is programmed to count a number of *Staphylococcus aureus* in the specimen.

* * * * *